US011738071B2

(12) United States Patent
Williams

(10) Patent No.: US 11,738,071 B2
(45) Date of Patent: Aug. 29, 2023

(54) TREATMENT OF ACUTE AND CHRONIC KIDNEY DISEASE

(71) Applicant: Penland Foundation, Beaumont, TX (US)

(72) Inventor: Roland M. Williams, Beaumont, TX (US)

(73) Assignee: Penland Foundation, Beaumont, TX (US)

(*) Notice: Subject to any disclaimer, the term of this patent is extended or adjusted under 35 U.S.C. 154(b) by 0 days.

(21) Appl. No.: 17/862,295

(22) Filed: Jul. 11, 2022

(65) Prior Publication Data

US 2023/0012181 A1 Jan. 12, 2023

Related U.S. Application Data

(60) Provisional application No. 63/220,966, filed on Jul. 12, 2021.

(51) Int. Cl.
*A61K 38/48* (2006.01)
*A61K 39/00* (2006.01)
*A61K 9/00* (2006.01)

(52) U.S. Cl.
CPC ........ *A61K 38/4893* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 5,766,605 A | 6/1998 | Sanders et al. | |
| 6,063,768 A | 5/2000 | First | |
| 6,139,845 A | 10/2000 | Donovan | |
| 6,143,306 A | 11/2000 | Donovan | |
| 6,261,572 B1 | 7/2001 | Donovan | |
| 6,337,075 B1 | 1/2002 | Donovan | |
| 6,632,440 B1 | 10/2003 | Quinn et al. | |
| 6,977,080 B1 | 12/2005 | Donovan | |
| 7,655,244 B2 | 2/2010 | Blumenfeld | |
| 8,470,337 B2 | 6/2013 | Manack et al. | |
| 8,734,810 B2 | 5/2014 | Blumenfeld | |
| 8,852,163 B2 | 10/2014 | Deem et al. | |
| 8,972,004 B2 | 3/2015 | Simon et al. | |
| 9,254,314 B2 | 2/2016 | Finzi et al. | |
| 9,707,207 B2 | 7/2017 | Finegold | |
| 10,011,823 B2 | 7/2018 | Barbieri et al. | |
| 10,258,673 B2 | 4/2019 | Pokushalov et al. | |
| 10,722,552 B1 | 7/2020 | Williams | |
| 10,960,061 B1 | 3/2021 | Williams | |
| 10,973,873 B1 | 4/2021 | Williams | |
| 10,987,441 B1 | 4/2021 | Sykes | |
| 2001/0012828 A1 | 8/2001 | Aoki et al. | |
| 2004/0062776 A1 | 4/2004 | Voet | |
| 2004/0213815 A1 | 10/2004 | Ackerman | |
| 2004/0220544 A1 | 11/2004 | Heruth et al. | |
| 2005/0147626 A1 | 7/2005 | Blumenfeld | |
| 2005/0191320 A1 | 9/2005 | Turkel et al. | |
| 2007/0259002 A1 | 11/2007 | Batchelor | |
| 2009/0142430 A1 | 6/2009 | Sanders et al. | |
| 2009/0232850 A1 | 9/2009 | Manack et al. | |
| 2010/0303788 A1 | 12/2010 | Francis et al. | |
| 2011/0200639 A1 | 8/2011 | Blumenfeld | |
| 2012/0093827 A1 | 4/2012 | Van Schaack et al. | |
| 2012/0195878 A1 | 8/2012 | Haag-Molkenteller et al. | |
| 2012/0244188 A1 | 9/2012 | Blumenfeld et al. | |
| 2012/0251519 A1 | 10/2012 | Blumenfeld et al. | |
| 2013/0251830 A1 | 9/2013 | Manack et al. | |
| 2014/0099298 A1 | 4/2014 | Blumenfeld | |
| 2015/0086533 A1 | 3/2015 | Borodic | |
| 2016/0095908 A1 | 4/2016 | Borodic et al. | |
| 2017/0173123 A1 | 6/2017 | Blumenfeld | |
| 2017/0333537 A9 | 11/2017 | Borodic | |
| 2018/0071361 A1 | 3/2018 | Abiad et al. | |
| 2019/0038646 A1 | 2/2019 | Bright et al. | |
| 2019/0300583 A1 | 10/2019 | Jarpe et al. | |
| 2020/0239528 A1* | 7/2020 | Binz | A61P 21/00 |
| 2021/0060144 A1 | 3/2021 | Brooks et al. | |
| 2021/0187063 A1 | 6/2021 | Williams | |
| 2022/0143158 A1 | 5/2022 | Abumrad et al. | |

FOREIGN PATENT DOCUMENTS

| | | |
|---|---|---|
| EP | 2072039 | 6/2009 |
| JP | 2007509953 | 4/2007 |
| JP | 2012107051 | 6/2012 |
| KR | 20100032982 | 3/2010 |
| KR | 20150126979 | 11/2015 |
| WO | 95/28171 | 10/1995 |
| WO | 00/10598 | 3/2000 |
| WO | 2010013495 | 2/2010 |
| WO | 2011084507 | 7/2011 |
| WO | 2012134897 | 10/2012 |
| WO | 2014184746 | 11/2014 |
| WO | 2018172264 | 9/2018 |
| WO | 2019126542 | 6/2019 |
| WO | 2019145577 | 8/2019 |
| WO | 2020110458 | 6/2020 |
| WO | 2022183064 | 9/2022 |

OTHER PUBLICATIONS

Understanding Different Types of Botulinum Toxin A, Harley Academy, pp. 1-5, Jul. 9, 2021.*
Sadick NS. Dermatol. Surg. 29: 348-350, 2003.*
Trizna Z. Dermatologic Use of Botulinum Toxin. Medscape, Feb. 6, 2019.*
Advance Nursing, "Angle of Injection," available online at: <https://nursing-skills.blogspot.com/2014/01/angle-of-injection.html>, 2 pages (2020).

(Continued)

*Primary Examiner* — S. Devi
(74) *Attorney, Agent, or Firm* — Fox Rothschild LLP

(57) ABSTRACT

A method for treating chronic kidney disease, or other renal conditions that has resulted in chronic low-grade activation of the cytokine system in a patient that is in need. Thereof comprising administering botulinum toxin to mitigate the inflammatory state in the kidney. A method of treating acute kidney disease that has resulted from an acute activation of the cytokine system in a patient in need thereof comprising administering nitrous oxide or any inhaled anesthetic in amounts, concentrations, and durations needed to control cytokines and mitigate further damage to healthy kidney tissue.

11 Claims, No Drawings

(56) References Cited

OTHER PUBLICATIONS

Chien et al., "Sympathetic Fiber Sprouting in Chronically Compressed Dorsal Root Ganglia Without Peripheral Axotomy," Author manuscript, published in final form as: J. Neuropathic Pain Symptom Palliation, 1(1), pp. 19-23, 7 pages (2005).

Children's Hospital of Pittsburgh, "Cirrhosis in Children: Symptoms and Treatment," available online at: <https://www.chp.edu/our-services/transplanUliver/education/liver-disease-states/cirrhosis>, 4 pages (2020).

Diel et al., "Photophobia and sensations of dryness in migraine patients occur independent of baseline tear volume and improve following botulinum toxin A injections," Author manuscript, published in final form as: Br. J. Ophthalmol., 103(8), pp. 1024-1029, 15 pages (2019).

Dobrek and Thor, "Glutamate NMDA Receptors in Pathophysiology and Pharmacotherapy of Selected Nervous System Dseases," Postepy Hig Med Dosw (online), 65, pp. 338-346 (2011).

Doherty, "The Link Between Migraines and Tinnitus, Buzzing or ringing in your ears could be related to your episodes," available online at: https://www.verywellhealth.com/link-between-migraines-and-tinnitus-4077631>, 13 pages (2019).

Espinosa-Sanchez and Lopez-Escamez, "New insights into pathophysiology of vestibular migraine," Frontiers in Neurology, 6(12), pp. 1-6 (2015).

Fernandez-Rodriguez et al., "Plasma Levels of Substance P in Liver Cirrhosis: Relationship to the Activation of Vasopressor Systems and Urinary Sodium Excretion," Hepatology, 21, pp. 35-40 (1995).

Fleischmann et al., "Nitrous oxide may not increase the risk of cancer recurrence after colorectal surgery: a follow-up of a randomized controlled trial" BMC Anesthesiology, 9 pages (2009).

Glatte et al., "Architecture of the Cutaneous Autonomic Nervous System," Frontiers in Neurology, 10(970), pp. 1-11 (2019).

Hart et al., "Chronic Pancreatitis: Managing a Difficult Disease," Am. J. Gastroenterol., 115(1), pp. 49-55 (2020).

Harvard Health Publishing, "Cardiac Arrhythmias, What is it?" available online at: <https://www.health.harvard.edu/a_to_z/cardiac-arrhythmias-a-to-z>; 5 pages (2019).

Herner et al., "Glutamate increases pancreatic cancer cell invasion and migration via AMPA receptor activation and Kras-MAPK signaling," Int. J. Cancer, 129(10), pp. 2349-2359 (2011).

Hulme and Snowling, "Reading disorders and dyslexia," Curr. Opin. Pediatr., 28, pp. 731-735 (2016).

Kandel et al., "Principles of Neurai Science," Third Edition, by Simon & Schuster, 1991; p. 218 (1991).

Kumar, "The Emerging Role of Botulinum Toxin in the Treatment of Orofacial Disorders: Literature Update," Asian J. Pharm Clin. Res., 10(9), pp. 21-29 (2017).

LeWitt and Trosch, "Idiosyncratic Adverse Reactions to Intramuscular Botulinum Toxin Type A Injection," Movement Disorders, 12(6), pp. 1054-1067 (1997).

Lim and Sheet, "Botulinum toxin, Quo Vadis?," Medical Hypotheses, 69, pp. 718-723 (2007).

Mayo Clinic, "Autism Spectrum Disorder," available online at: <https://www.mayoclinic.org/diseases-conditions/autism-spectrum-disorder/symptoms-causes/syc-20352928?p=1, 5 pages (2019).

Mayo Clinic, "Epilepsy," available online at: <https://www.mayoclinic.org/diseases-conditions/epilepsy/diagnosis-treatment/drc-20350098>, 8 pages (2022).

Mazzone and Undem, "Vagal Afferent Innervation of the Airways in Health and Disease," Physiol. Rev., 96, pp. 975-1024 (2016).

Mitchell and Borasio, "Amyotrophic lateral sclerosis," Lancet 369: pp. 2031-2041 (2007).

Monroy et al., "The Use of Botulinum Toxin-A in the Treatment of Severe Bruxism in a Patient with Autism: A Case Report," Special Care in Dentistry, 26(1), pp. 37-39 (2006).

Mortazavi et al., "Xerostomia Due to Systemic Disease: A Review of 20 Conditions and Mechanisms," Ann. Med. Health Sci. Res., 4(4), pp. 503-510 (2014).

Nair et al., "Impaired thalamocortical connectivity in autism spectrum disorder: a study of functional and anatomical connectivity," Brain, A Journal of Neurology, 136, pp. 1942-1955 (2013).

National Istitutes of Health "Juvenile Amyotrophic Lateral Sclerosis," found online at: <https://rarediseases.info.nih.govtdiseasesi11901/juveniie- amyotrophic-lateral-sclerosis>, 8 pages (2020).

Oomens and Forouzanfar, "Pharmaceutical Management of Trigeminal Neuraigia in the Elderly," Drugs Aging, 32, pp. 717-726 (2015).

Panju et al., "Atypical Sympathetic Arousal in Children with Autism Spectrum Disorder and its Association with Anxiety Symptomatology," Molecular Autism, 6(64), 10 pages (2015).

Park and Park, "Botulinum Toxin for the Treatment of N europathic Pain," Toxins, 9(260), 15 pages (2017).

Powell et al., "The Role of CGRP in Tile Development of Morphine Tolerance and Physical Dependence," 4th International Meeting on Calcitonin Gene-Related Peptide (CGRP), The Scientific World 1(S1), 1 page (2001).

Pugh et al., "Glutamate and choline levels predict individual differences in reading ability in emergent readers," J. Neurosci., 34(11), pp. 4082-4089 (2014).

Ristic, "7 Proven Roles of Substance P and its Associated Diseases," available online at: https://supplements.selfdecode.com/blog/substance-p-roles/>, 9 pages (2021).

Rojas, "The role of glutamate and its receptors in autism and the use of glutamate receptor antagonists in treatment," Author manuscript, published in final form as: J. Neural. Transm., 121(8), pp. 891-905 (2014).

Sarawagi et al., "Glutamate and GABA Homeostasis and Neurometabolism in Major Depressive Disorder," Frontiers in Psychiatry, 12(637863), pp. 1-16 (2021).

Saunte and Christensen, "Improvement in readingsymptoms followingbotulinum toxin A injectionfor convergenceinsufficiency typeintermittent exotropia," Acta Opthalmologica 93(5), pp. e391-e392 (2015).

Scott and Fryer, "Role of Parasympathetic Nerves and Muscarinic Receptors in Allergy and Asthma,"Author manuscript, published in final form as: Chem. Immunol. Allergy, 98: pp. 48-69 (2012).

Shimmura et al., "Alteration of Plasma Glutamate and Glutamine Levels in Children with High-Functioning Autism," PLoS ONE, 6(10), 6 pages (2011).

Smith, "Hyperhidrosis," Vascular Surgery, 31(5), pp. 251-255 (2015).

Squires et al., "The Use of Botulinum Toxin Injections to Manage Drooling in Amyotrophic Lateral Sclerosis/Motor Neurone Disease: A Systematic Review," Dysphagia, 29, pp. 500-508 (2014).

Strobl et al., "Best Clinical Practice in Botulinum Toxin Treatment for Children with Cerebral Palsy," Toxins, 7, pp. 1629-1648 (2015).

Vacca et al., "Botulinum toxin A increases analgesic effects of morphine, counters development of morphine tolerance and modulates glia activation and μ opiod receptor expression in neuropathic mice," Brain, Behavior, and Immunity, 32, pp. 40-50 (2013).

Veenstra-VanderWeele et al., "Arbaclofen in Children and Adolescents with Autism Spectrum Disorder: A Randomized, Controlled, Phase 2 Trial," Neuropsychopharmacology, 42, pp. 1390-1398 (2017).

WebMD, "ADHD and Dyslexia: How to Tell Them Apart," available online at: <https://www.webmd.com/add-adhd/adhd-dyslexia-tell-apart?print=true>, 3 pages (2020).

WebMD, "Treatments for Dyslexia," available online at: <https://www.webmd.com/children/dyslexia-treatments?print=true>, 1 page (2020).

What-When-How, "Neuroscience," available online at: <http://what-when-how.com/neuroscience> 2 pages (2020).

Wijesekera and Leigh, "Amyotrophic lateral sclerosis," Orphanet Journal of Rare Diseases, 4(3), 22 pages (2009).

U.S. Appl. No. 17/880,962, filed Aug. 4, 2022, Botulinum Toxin for Use in Treatment.

U.S. Appl. No. 17/204,922, filed Mar. 17, 2021, Treatment of Dyslexia Using Botulinum Toxin.

U.S. Appl. No. 17/987,549, filed Nov. 15, 2022, Treatment of Asthma Using Botulinum Toxin.

U.S. Appl. No. 17/987,626, filed Nov. 15, 2022, Treatment of Chronic Obstructive Pulmonary Disease Using Botulinum Toxin.

(56) References Cited

OTHER PUBLICATIONS

U.S. Appl. No. 17/987,653, filed Nov. 15, 2022, Treatment of Cardiac Arrhythmia Using Botulinum Toxin.
U.S. Appl. No. 17/215,082, filed Mar. 29, 2021, Treatment of Amyotrophic Lateral Sclerosis Using Botulinum Toxin.
U.S. Appl. No. 17/987,675, filed Nov. 15, 2022, Treatment of Cirrhosis Using Botulinum Toxin.
U.S. Appl. No. 17/862,282, filed Jul. 11, 2022, Treatment of Diabetes and Chronic Pancreatitis Using Botulinum Toxin.
U.S. Appl. No. 16/657,933, filed Oct. 18, 2019, Treatment of Autism Using Botulinum Toxins.
U.S. Appl. No. 17/525,367, filed Nov. 12, 2021, Botulinum Toxin for Use in Treatment of Autism Spectrum Disorders.
U.S. Appl. No. 16/995,042, filed Aug. 17, 2020, Treatment Methods Using Botulinum Toxins.
U.S. Appl. No. 16/875,912, filed May 15, 2020, Treatment of Dyslexia Using Botulinum Toxin.
U.S. Appl. No. 16/875,924, filed May 15, 2020, Treatment of Asthma Using Botulinum Toxin.
U.S. Appl. No. 16/875,935, filed May 15, 2020, Treatment of Chronic Obstructive Pulmonary Disease Using Botulinum Toxin.
U.S. Appl. No. 16/875,945, filed May 15, 2020, Treatment of Cardiac Arrhythmia Using Botulinum Toxin.
U.S. Appl. No. 16/875,947, filed May 15, 2020, Treatment of Amyotrophic Lateral Sclerosis Using Botulinum Toxin.
U.S. Appl. No. 16/875,951, filed May 15, 2020, Treatment of Cirrhosis Using Botulinum Toxin.

\* cited by examiner

TREATMENT OF ACUTE AND CHRONIC KIDNEY DISEASE

PRIORITY CLAIM

The application is based on and claims priority to U.S. Provisional Application No. 63/220,966, filed Jul. 12, 2021, which is expressly incorporated herein by reference thereto.

This application is also related by ownership to the following cases, filed on Oct. 18, 2019: TREATMENT OF AUTISM USING BOTULINUM TOXINS, Ser. No. 16/657,933, now U.S. Pat. No. 10,722,552; filed on Oct. 18, 2019: TREATMENT OF NARCOTICS TOLERANCE USING BOTULINUM TOXINS, Ser. No. 16/657,950, now abandoned; filed on Aug. 17, 2020: TREATMENT METHODS USING BOTULINUM TOXINS, Ser. No. 16/995,042, now U.S. Pat. No. 11,241,479; filed on May 15, 2020: TREATMENT OF DYSLEXIA USING BOTULINUM TOXIN, Ser. No. 16/875,912, now U.S. Pat. No. 10,967,052; filed on Aug. 17, 2020: TREATMENT OF ASTHMA USING BOTULINUM TOXIN, Ser. No. 16/995,042, now U.S. Pat. No. 11,241,479; filed on May 15, 2020: TREATMENT OF CHRONIC OBSTRUCTIVE PULMONARY DISEASE USING BOTULINUM TOXIN, Ser. No. 16/875,935, now U.S. Pat. No. 10,987,411; filed on May 15, 2020: TREATMENT OF CARDIAC ARRHYTHMIA USING BOTULINUM TOXIN, Ser. No. 16/875,945, now U.S. Pat. No. 10,960,060; filed on May 15, 2020: TREATMENT OF CIRRHOSIS USING BOTULINUM TOXIN, Ser. No. 16/875,951, now U.S. Pat. No. 11,090,371; filed on May 4, 2022: TREATMENT OF ARDS AND OTHER CONDITIONS CAUSED BY ACUTELY ELEVATED CYTOKINE LEVELS AND POST ARDS CHRONIC CYTOKINE PRODUCTION USING INHALED ANESTHETICS, Ser. No. 17/662,068.

TECHNICAL FIELD

Embodiments of the present invention generally relate to a method of treating acute and chronic kidney disease and other renal conditions by mitigating an acute or chronic activation of the cytokine system.

DESCRIPTION OF RELATED ART

Kidney disease is a major health problem in the United States, afflicting nearly eight million Americans. Kidney disorders run the gamut from minor infections to total kidney failure, and can cause fluid and electrolyte disturbance, high blood pressure, anemia, bone metabolic disease, elevated cholesterol and heart disease. When chronic, it can lead to depression and sexual dysfunction.

SUMMARY

Cytokine production is a normal part of infection control and damage repair. However, if overproduced, acutely or chronically, it can damage or destroy normal kidney tissues. Substance P activates the NK-1-3 receptors on immune cells, triggering the release of cytokines. Nitrous oxide or any inhaled anesthetics can mitigate the overproduction of acute levels of substance P. This can suppress and control the acute cytokine damage to the kidney in acute kidney disease (AKD). Botulinum toxin by its ability to selectively stop only the chronic overproduction of substance P in the neurostructural cells or the sensory ganglion mitigate the chronic inflammation and stop the progressive loss of kidney function in chronic kidney disease (CKD).

The claimed disclosure is related to methods for treating and mitigating the effects of extreme spikes in the levels of substance P after an acute injury to the kidney. Any injury can result in a severe pathological elevation of the cytokines (cytokine storm). This extreme reaction can damage the normal tissue in the kidney. In some cases, the cytokine damage can be worse than the original insult. Embodiments of the present invention involve treatment for acute kidney disease (AKD) that involves administering nitrous oxide.

In some embodiments, the method comprises administering an anesthetic to the patient by inhalation, thereby treating the conditions.

In some embodiments, the inhaled anesthetic comprises isoflurane, sevoflurane, desflurane, nitrous oxide, xenon, or a combination thereof.

In some embodiments, the inhaled anesthetic includes nitrous oxide and oxygen. A composition of the inhaled anesthetics may be from about 1% nitrous oxide/about 99% oxygen to about 70% nitrous oxide/about 30% oxygen. A composition of the inhaled anesthetic may be from about 40% nitrous oxide/about 60% oxygen to about 50% nitrous oxide/about 50% oxygen. A composition of the inhaled anesthetic may be about 50% nitrous oxide/about 50% oxygen.

In some embodiments, the inhaled anesthetics is provided to an adult who weighs about 150 lbs. between about for 1 minute every 4 hours and continuous administration.

In some embodiments, a duration, an interval, and a total amount of inhaled anesthetics provided to an adult, or a child is adjusted for age, weight, or a combination thereof.

In some embodiments, a composition, duration, an interval, and a total amount of inhaled anesthetics provided to an adult, or a child is adjusted for age, weight, need, or a combination thereof.

Furthermore, the disclosure is related to methods for treating or mitigating the effects of chronic long-term overproduction of substance P. This chronic excess production of substance P triggers immune cells to constantly secrete varying low-level cytokines. The resulting chronic inflammatory state slowly and progressively damages and destroys the kidney (CKD).

In some embodiments, the method comprises administering a botulinum toxin to the patient by subcutaneous or intradermal injection, 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the spine, 1-4 units to and/or around the vicinity of a lumbar nerve, lateral to the spine, and/or 1-4 units to and/or around the vicinity of a sacral nerve, lateral to the spine, thereby treating the conditions.

In some embodiments, the trigeminal nerve is selected from the group consisting of an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, a lesser occipital nerve, a greater occipital nerve, or a combination thereof.

In some embodiments, the cervical nerve is selected from the group consisting of a c-2 nerve, c-3 nerve, c-4 nerve, c-5 nerve, c-6 nerve, c-7 nerve, c-8 nerve, or a combination thereof.

In some embodiments, the thoracic nerve is selected from the group consisting of t-2 to t-3, t-5 to t-6, t-7 to t-9, t-10 to t-12, or a combination thereof.

In some embodiments, the sacral nerve is selected from the group consisting of s-1 to s-2, s-3 to s-4, and/or s-4 to s-5, or a combination thereof.

In some embodiments, the botulinum toxin is selected from the group consisting of botulinum toxin type A, botulinum toxin type B, botulinum toxin type C, botulinum toxin type D, botulinum toxin type E, botulinum toxin type F, and botulinum toxin type G, a fragment thereof, a hybrid thereof, a chimera thereof, or a combination thereof.

In some embodiments, the therapeutically effective amount of the botulinum toxin administered is between about 1 unit and about 150 units. The therapeutically effective amount can be about 1 to about 50 units, about 1 to about 30 units, about 50 to about 100 units, about 1 to about 60, about 6 to about 60, and about 50 to about 150. In some instances, the therapeutically effective amount of botulinum toxin can be about 1 (or 2) to about 4 units.

In some embodiments, a total dosage of the botulinum toxin to an adult who weighs about 150 lbs. is less than or equal to about 50 units, and the total dosage of the botulinum toxin in an adult is adjusted for weight, and wherein a total dosage of the botulinum toxin in a child over about 5 years old and a toddler about from 1 to 5 years old is adjusted for age, weight or a combination thereof.

In some embodiments, each of the subcutaneous or intradermal injections is bilateral.

In some embodiments, the patient is administered 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2, 1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral).

In some embodiments, treatment is administered comprising botulinum toxin and/or nitrous oxide treatment described herein.

DETAILED DESCRIPTION OF THE PREFERRED EMBODIMENTS

Further in relation to this, before explaining at least the preferred embodiments of the disclosure in greater detail, it is to be understood that the disclosure is not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any dictionary definition of such term, it is intended that the meaning of the term as understood by the ordinary artisan will prevail.

As used herein, the term "about" means approximately or nearly and in the context of a numerical value or range set forth herein means±10% of the numerical value or range recited or claimed.

The term "treating" includes delaying, alleviating, mitigating, or reducing the intensity, progression, or worsening of one or more attendant symptoms of a disorder or condition and/or alleviating, mitigating, or impeding one or more causes of a disorder or condition. Treatment under the claimed disclosure may be a preventative treatment, prophylactic treatment, remission of treating, or ameliorating treatment.

The term "therapeutically effective amount" or "therapeutically effective dose" refers to the amount of a composition, compound, therapy, or course of treatment that, when administered to an individual for treating a disorder or disease, is sufficient to affect such treatment for the disorder or disease. The "therapeutically effective amount" will vary depending on the composition, the compound, the therapy, the course of treatment, the disorder or disease and its severity, and the age, weight, etc., of the individual to be treated.

The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

As used herein, "consists essentially of" when used in conjunction with a composition means excluding other materials that contribute to mitigating cytokine overproduction, thereby treating chronic and acute kidney disease, and other renal conditions that have resulted from the overproduction of cytokines. The objective of administering botulinum toxin and/or inhaled anesthetic is to treat the conditions by mitigating cytokine overproduction. With the language, other materials that contribute to the treatment that materially affect the basic and novel characteristics of the disclosure are not required and are potentially counterproductive because they may offset the treatment effect of botulinum toxin and/or inhaled anesthetic. In other words, the meaning of "consists essentially of" is tied to the objective and excludes materials (that contribute to the treatment) that are pharmaceutically active for the treatment and materially mitigate cytokine overproduction and thereby affecting the treatment of the conditions. Small traces that have little or no effect to the treatment as part of the embodiments of the presentation disclosure may exist in a composition that consists essentially of botulinum toxin and/or inhaled anesthetic under the definition because it would not materially affect its function and/or objective.

In accordance with the principles of the present disclosure, use of nitrous oxide is recommended to treat acute kidney disease that results in excess activation of the cytokine system (cytokine storm). Botulinum toxin is used to treat chronic kidney disease.

Substance P in Acute and Chronic Kidney Disease

Numerous studies have shown elevated levels of Substance P and the resulting cytokine increase in the kidney and blood of patients with chronic and acute kidney disease. Substance P activates NK-1 receptors on Immune cells which are stimulated to release cytokines.

In chronic kidney failure, the neurostructural cells in the dorsal root and vagal ganglia constantly release substance P, and the resulting chronic low-grade cytokine induced inflammation slowly destroys the kidney.

In acute kidney disease, an injury to the kidney damages the sensory nerves in the kidney. This results in a sudden extreme level of substance P release. The resulting extreme level of cytokine causes immediate severe damage to the kidney. What is needed is a way to stop the chronic progressive low-grade damage to the kidney in chronic kidney disease, and a way to stop extreme cytokine damage to the kidney in acute kidney failure while the damaging condition that caused the damage is managed. Current treatments are marginally effective.

Cytokines/Cytokine Storm

Cytokines are a diverse group of small proteins and peptides that, among other functions, regulate and participate in the initial response to infection. Some have antibacterial and antiviral properties, some suppress viral and bacterial reproduction, some destroy infected cells and tissue, and others raise body temperature to suppress and slow the infection until antibody production begins.

The major types of cytokines are interferons, interleukins, chemokines, colony-stimulating factors, and tumor necrosing factors. There are hundreds of different peptides under these major classes that damage, kill, or slow the growth of invading bacteria or viruses. They are the body's version of chemotherapy. However, this comes at the cost of some collateral damage. The stronger the cytokine reaction, the more damage to healthy tissue. Some of the body's own tissue is damaged or destroyed by the cytokine reaction.

In acute or chronic kidney problems, the cytokine reaction is initially triggered by viral or bacterial proteins, cellular damage from injury, toxins, drugs, heat stroke, etc. Later, a much larger amount of substance P is produced and released by the sensory neurons in response to damage from literally any source with a resulting cytokine reaction. If an acute level of cytokine production occurs, the damage can be worse than the original one. Other times, chronic low-grade damage from drugs, smoking, alcohol use, chronic infection, etc. can cause chronic low-grade substance P production with corresponding levels of cytokines that slowly damage and destroy the kidney. The half-life of most cytokines is seconds to minutes. The cells that produce them must be constantly stimulated to produce them.

Chronic Kidney Disease

Chronic kidney disease (kidney failure) is recognized by its signs and symptoms, including fatigue, swelling of the feet and legs (edema), pain or sensitivity around the middle to lower back and sides of the abdomen, nausea, vomiting, loss of appetite, anemia, changes in sexual drive, and confusion. Limitation of physical activity due to chronic kidney disease often leads to reduction in physical activity.

Initiating factors of chronic kidney disease include alcohol use, smoking, chronic infection, diabetes, high blood pressure, glomerulonephritis, and polycystic kidney disease, with factors such as genetics playing a smaller role.

Chronic kidney disease affected 753 million men and women globally in 2016. Studies have shown that blood and kidney levels of substance P are elevated in CKD. The chronic cytokine production from the immune cells in the kidney from the elevated substance P causes chronic damage to the kidneys. The rate of progression of CKD depends on how elevated substance P levels are above normal and the kidney's ability to heal from the damage.

Diagnosis of chronic kidney disease is normally found in normal blood tests and should be considered in anyone exhibiting the signs and symptoms, or anyone seeing a specialist for medical issues involving the endocrine system. Screening those who are considered at-risk is imperative in diagnosing this disease before too much damage occurs. Initial treatments may include medications to lower blood pressure, blood sugar, and/or cholesterol. Medications may include angiotensin converting enzyme inhibitors (ACEIs), angiotensin II receptor antagonists (ARBs), or loop diuretics. NSAIDs and high-sodium foods should be avoided, the number of ingested proteins should be regulated, and proper physical activity should be implemented to control symptoms of chronic kidney failure and renal distress.

Chronic kidney disease can develop over months to years and is often preceded by urinary tract and kidney infections, problems with water retention and expulsion, and high blood pressure, high blood sugar, and cholesterol. Renal failure is a medical emergency and can lead to death if it is not properly treated in time. Hemodialysis, peritoneal dialysis, and kidney transplants are the last medical treatments available to those suffering from end stage chronic kidney disease.

Treatment of CKD

Numerous clinical studies have shown the serum and intra kidney levels of substance P is elevated in CKD. If a patient is diagnosed to experience chronic kidney disease, he or she can be given botulinum toxin subcutaneously or by any other injection that allows any of the botulinum toxins to reach the unmyelinated sensory C-fiber (e.g., intradermal injection, etc.) to prevent or alleviate chronic substance P production with the resulting chronic cytokine production.

The patient may be given botulinum toxin subcutaneously or by any other injection that allows the botulinum toxin to reach the unmyelinated sensory C fiber (e.g., intradermal injection, etc.) to prevent or alleviate their chronic inflammatory conditions. Blood tests to assess blood levels of substance P may be performed to confirm the elevated levels have returned to normal. Because the sensory innervations of the internal organs originate from the vagus ganglia and spinal dorsal root ganglia the botulinum toxin injection can be given to and/or around the vicinity of a trigeminal nerve, a cervical nerve, a thoracic nerve, a lumbar nerve, sacral nerve, or a combination thereof of the patient. Preferably, it is not necessary to inject botulinum toxin directly to the vagus nerves because there is numerous anastomosis between the trigeminal nerves and the spinal nerves. The selected trigeminal nerve may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve minimizes or eliminates muscular side effects. The selected cervical nerve may include, but is not limited to, the c-2 nerve, c-3 nerve, c-4 nerve, c-5 nerve, c-6 nerve, c-7 nerve, c-8 nerve, or a combination thereof. The selected thoracic nerve may include, but is not limited to, the t-2 to t-3 nerve, t-5 to t-6 nerve, t-7 to t-9 nerve, and/or t-10 to t-12 nerve, or a combination thereof. The selected lumbar nerve may include, but is not limited to, the 1-1 to 1-2 nerve, 1-2 to 1-3 nerve, and/or 1-4 to 1-5 nerve, or a combination thereof. The selected sacral nerve may include, but is not limited to, the s-1 to s-2, s-3 to s-4, and/or s-4 to s-5, or a combination thereof. For example, 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2, 1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral) can be administered. While the administration site is about one-inch lateral to the patient's spine in the above embodiment, the distance can be more than 0 inches, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present disclosure are preferably applied to all or many of these locations. Depending on symptoms or conditions, the botulinum toxin used in embodiments of the present disclosure can be injected to a subset or subgroup of the locations described in embodiments of the present disclosure. In one embodiment, 3 injections of 2 units each distributed along each side of the neck in the cervical area on the trigeminal nerve, 1 injection of 2 units in the ophthalmic, maxillary, mandibular division subcutaneously and bilaterally. These dosages are for an adult who weighs about 150 lbs. The dosage for an adult or a child with asthma would have to be adjusted for age, weight, or a combination thereof.

Botulinum toxin is given to lower the levels of substance P and CGRP, and botulinum toxin to normal levels. It normally begins to work in 3-7 days.

In general, the total dosage or amount can be, for example, 1-150 units depending on the patient's body weight. Preferably, the total dosage is about 20-150 units. Preferably, the total dosage for adults whose weight is 150 lbs. is less than or equal to about 50 units (about 1 to 50 units inclusive of endpoints). In some embodiments, the total dosage for adults whose weight is 150 lbs. is about 50-150 units. For an adult or a child, the dosage can be adjusted to the patient's body weight, age, or a combination thereof. For toddlers (e.g., from about 1 to 5 years old), the dosage can be, for example, about 1-30 units and can be adjusted to the patient's body weight and age. This is an estimate, but 30 units is the maximum dosage that has been used safely since the 1990s in cerebral palsy infants and young children to control their severe muscle spasms.

Botulinum toxin is given to lower the levels of substance P and CGRP, and botulinum toxin normally begins to work after about three days. It normally takes the botulinum toxin about one to two weeks to reach the height of its effectiveness. Blood levels of substance P and CGRP can be monitored to make sure that the levels drop to normal, and the patient's physical symptoms can be monitored to make sure the levels normalize as well. When the botulinum toxin wears off, blood tests show an increase in substance P or CGRP, and/or the symptoms begin to redevelop, botulinum toxin can be given again to combat the symptoms of the condition. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

Botulinum toxin cleaves the SNAP25 and/or VAMP at the neuro muscular junction in muscles this causes the clinical effects of botulinum toxin. The resulting paralyzed muscles last for 3-4 months until the cell grows a new protein. This effect has been used for decades for overactive muscles (such as treating overactive muscles as part of cervical dystonia, blepharospasm, tic's, Parkinson's, cerebral palsy, wrinkles in the face, excessive sweating, and overactive bladder.) In the sensory nerves, the mechanism has been used for treating migraines and depression. The effect of blocking the SNAP25 and/or VAMP in the glial, satellite, and astrocyte cells will work for 2-9 months until these cells grow new proteins. The important part of this mechanism is that the botulinum effect does not destroy cells and does not stop the normal production of or effects of acetylcholine (muscles) or substance P, CGRP, or glutamate in sensory nerves. These facts give huge advantages over a monoclonal antibody which would eliminate all glutamate, CGRP, and substance P. Side effects of such elimination would be disastrous. The receptor antagonists also have problems, because they are not site-specific, they block glutamate, substance P, and CGRP everywhere. Too little glutamate, substance P, and CGRP is a problem, as well as too much. It is difficult to regulate oral or I.V. doses to obtain the correct level of reduction in areas that are too high in glutamate, substance P, and/or CGRP without over-reduction in areas with normal levels.

Small doses of botulinum toxin injected into a specific muscle can deactivate the SNAP25 and/VAMP to calm the muscle's overreaction or paralyze the muscle temporarily if desired. If injected subcutaneously near unmyelinated sensory nerves, the botulinum toxin can stop the overproduction of the sensory neuro excitatory compounds without affecting normal glutamate, substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage, and injection must be done with knowledge and care.

In particular, the mechanism of the sensory effect (stopping overproduction of glutamate, substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low doses of botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess substance P, CGRP, and glutamate, which is involved in a response mechanism to neural injury without affecting normal glutamate, substance P, and CGRP production, use, or receptors. An example of the neural injury mechanism dysfunction is a shingles infection. The infection by the shingles virus damages the nerve but does not kill it, or there would be no feeling (numbness). This causes a spike in the production of glutamate, substance P, and CGRP. This causes the well-known shingles pain and hypersensitivity. Over a 2-3 month period, the infection is controlled, the nerve heals, and the overproduction of the neuro excitatory chemicals gets back to normal. However, sometimes for unknown reasons, the overproduction does not get back to normal but remains high, and severe chronic pain and hypersensitivity persists. Chronically over stimulated neurons can cause numerous problems depending on where the neurons are located. The neuro excitatory chemicals can travel up the spinal cord to the brain in the CSF and affect neurons there. This process is called central sensitization.

Botulinum toxins for use according to the present disclosure can be stored in lyophilized, vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the aforementioned nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and can include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al *Therapy with Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily affects neural systems believed to be involved in a selected neuropsychiatric disorder and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

Novel Location and Injection Techniques to Mitigate or Eliminate Muscular Side Effects of Botulinum Toxin while Controlling the Overproduction of Substance P, Glutamate, and CGRP 1. Subcutaneous Injection The subcutaneous injections allow for the botulinum toxin to diffuse into the unmyelinated C-fibers and pass by diffusion up to the ganglia where it renders non-functional the SNAP-25 protein in the neurostructural cells (astrocyte, glial, and satellite). This blocks the release of substance P, glutamate, and CGRP into the spinal fluid surrounding the neuron. This mechanism blocks only the overproduction of substance P and glutamate while not interfering with the normal production and use of these vital neurotransmitters. Neurons have receptors on their surfaces that are activated by substance P, glutamate, and CGRP. Immune cells have substance P reception (NKI-3) that activates immune cells to produce cytotoxicity. With intramuscular injections, the botulinum toxin must diffuse through the muscle, fibrous tissue, and myelin to reach the motor neuron and block the acetylcholine. The unmyelinated C-fibers in the skin allow the botulinum toxin to diffuse into the neuron more efficiently than myelin protected neurons in the muscles.

2. Injection Site ½ Inch Lateral to the Spine

When the botulinum toxin is given subcutaneously, it must diffuse up the C-fiber axon by passive diffusion. This is a very slow process, and the botulinum toxin can degrade on the journey. In known published early trials, botulinum toxin used for fibromyalgia is 25 units per injection given over trigger points in the forearm and calf. This only covered the injected dermatomes and took 2-3 weeks to diffuse up the axon and reach the ganglia. This problem was addressed by giving the subcutaneous injections approximately ½ inch lateral to the spine. The site of excess substance P, glutamate and CGRP is in the neuro structural cells of the dorsal root and vagal sensory ganglia. The botulinum toxin must only diffuse approximately 1 inch rather than several feet. This allowed us to use only 2 units of botulinum toxin, diffusion time is 3-5 days, due to anastomosis among the spinal sensory nerves in this area, this injection technique covers 2-3 dermatomes. The lessened time and distance also allow for less time for degradation of the Botulinum Toxin.

3. Vagus Nerve Injection

The Vagus nerve is a spinal nerve that exits the base of the skull and travels down the throat to the internal organ it supplies (parasympathetic, motor, and sympathetic innervations to the throat and internal organs). The vagus nerve's only superficial innervations is a nerve called Arnold's nerve that innervates the skin in the external ear. At this location it is a mixed motor and sensory nerve. The motor component innervates the throat muscles. Injection in this area could cause muscle weakness or paralysis in the throat. Studies show that there are numerous anastomoses between the trigeminal and cervical sensory nerves and the vagus sensory nerves. Subcutaneous botulinum toxin injection in the trigeminal and cervical dermatomes allows for diffusion through these anastomoses to the sensory vagal nerves to reach the sensory vagal ganglia with botulinum toxin and prevent the overproduction of only substance P, glutamate, and CGRP. This minimizes or eliminates vagus nerve motor side effects. This also eliminates the complicated and potentially dangerous injections directly to the vagus ganglia.

4. Mitigated or Eliminate Spinal Motor Side Effect

The injection location approximately ½ inch lateral to the spine is the only location in the body where the sensory and motor systems are truly separated. In the spinal cord, the motor and sensory nerves are in very close proximity; however, when they exit the spinal column the sensory nerves exit as the dorsal root and the motor nerves exit in the ventral root. Then lateral to the spine, they unite and form a mixed nerve. At this injection point ½ inch lateral to the spine, the sensory nerves are separated by bone and connective tissue preventing diffusion to the motor nerves in the ventral root and mitigating or eliminating motor side effects.

Botulinum toxin is given to lower the levels of substance P, CGRP, and glutamate, and it normally begins to work after about three days. The injection is about ½ to an inch from the spinal cord for all spinal injections. Published early studies gave described injections in the forearm or calf, and it was found to take about two weeks to begin working, In contrast, when the injection is given near the dorsal root ganglion, the toxin normally only takes 3-5 days and 1 to less than 2 weeks to reach the height of its effectiveness. This is because it is a shorter distance to diffuse up the axon to the cell body. Blood glutamate levels can be monitored to make sure the levels drop to normal, and the chronic kidney disease symptoms can be monitored to make sure they normalize as well.

In general, the dosage can be between 1-150 units depending on the patient's body weight. The dosage for adults whose weight is about 150 lbs. is about 50-150 units. For those who are underweight with a low Body Mass Index, the dosage can be adjusted to the patient's body weight. Botulinum toxins for use according to the present disclosure can be stored in lyophilized, vacuum dried form in containers under vacuum pressure or as stable liquids. Prior to lyophilization, the botulinum toxin can be combined with pharmaceutically acceptable excipients, stabilizers, and/or carriers, such as albumin. The lyophilized material can be reconstituted with saline or water to create a solution or composition containing the botulinum toxin that is to be administered to the patient.

Preferably, the botulinum neurotoxin is peripherally administered by giving it to or in the vicinity of the aforementioned nerve or nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and can include implantation of a controlled release system that controllably releases the botulinum neurotoxin to the target trigeminal tissue. Such controlled release systems reduce the need for repeat injections. Diffusion of biological activity of a botulinum toxin within a tissue appears to be a function of dose and can be graduated. (Jankovic J., et al *Therapy With Botulinum Toxin*, Marcel Dekker, Inc., [1994], page 150). Thus, diffusion of botulinum toxin can be controlled to reduce potentially undesirable side effects that may affect the patient's cognitive abilities. For example, the botulinum neurotoxin may be administered so that it primarily affects neural systems believed to be involved in a selected neuropsychiatric disorder and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor), and/or a translocation domain. By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin is selected from the group consisting of botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depending on the type of botulinum toxin. The botulinum toxin can be used with other modulating drugs or chemicals. In further embodiments, the therapeutically effective amount of the botulinum toxin administered is between about 1 unit and about 150 units.

Acute Kidney Failure (Injury)

Acute Kidney Injury (AKI), previously called Acute Renal Failure (ARF), is an acute physical ailment compared to Chronic Kidney Disease (CKD). It is a sudden decrease in kidney function that develops within 7 days, as shown by an increase in serum creatinine or a decrease in urine output, or both. Whatever the cause of AKI, renal blood flow reduction is a common pathologic pathway for declining glomerular filtration rate. Pathophysiology of AKI has always been traditionally divided into three categories: prerenal, renal, and post-renal. Each of these categories has several different causes associated with it.

The prerenal form of AKI begins with any cause of reduced blood flow to the kidney. This may be part of systemic hypoperfusion resulting from hypovolemia or hypotension or maybe due to selective hypo perfusion to the kidneys, such as those resulting from renal artery stenosis and aortic dissection. However, tubular and glomerular function tends to stay normal. A few examples with the mechanism of prerenal AKI are listed below:

1. Hypovolemia: hemorrhage, severe burns, and gastrointestinal fluid losses such as diarrhea, vomiting, high ostomy output.
2. Hypotension from the decreased cardiac output: cardiogenic shock, massive pulmonary embolism, acute coronary syndrome.

3. Hypotension from systemic vasodilation: septic shock, anaphylaxis, anesthesia administration, hepatorenal syndrome.
4. Renal vasoconstriction: NSAIDs, iodinated contrast, amphotericin B, calcineurin inhibitors, hepatorenal syndrome.
5. Glomerular efferent arteriolar vasodilation: ACE inhibitors, angiotensin receptor blockers.

Intrinsic renal causes include conditions that affect the glomerulus or tubule, such as acute tubular necrosis and acute interstitial nephritis. This underlying glomerular or tubular injury is associated with the release of vasoconstrictors from the renal afferent pathways. Prolonged renal ischemia, sepsis, and nephrotoxins being the most common ones. It is worth mentioning that prerenal injury can convert into a renal injury if the offending factor's exposure is prolonged enough to cause cellular damage. Few examples of this mechanism are listed below:

1. Acute tubular necrosis: ischemia from prolonged pre-renal injury, drugs such as aminoglycosides, vancomycin, amphotericin B, pentamidine; rhabdomyolysis, intravascular hemolysis.
2. Acute interstitial nephritis: Drugs such as beta-lactam antibiotics, penicillin's, NSAIDs, proton pump inhibitors (PPIs), 5-ASA; infections, autoimmune conditions (SLE, IgG related disease).
3. Glomerulonephritis: anti-glomerular basement membrane disease, immune complex-mediated diseases such as SLE, post-infectious glomerulonephritis, cryoglobulinemia, IgA nephropathy, Henoch-Schonlein purpura.
4. Intratubular obstruction: monoclonal gammopathy seen in multiple myeloma, tumor lysis syndrome, toxins such as ethylene glycol.

Prerenal causes of AKI include sepsis, dehydration, excessive blood loss, cardiogenic shock, heart failure, cirrhosis, and certain medications like ACE inhibitors or NSAIDs. Intrinsic renal causes of AKI include glomerulonephritis, lupus nephritis, acute tubular necrosis, certain antibiotics, chemotherapeutic agents, and contrast dye used for imaging. Postrenal causes of AKI include kidney stones, bladder cancer, neurogenic bladder, enlargement of the prostate, narrowing of the urethra, and certain medications like anticholinergics.

Post-renal causes mainly include obstructive causes, which lead to congestion of the filtration system leading to a shift in the filtration driving forces. The most common ones are renal/ureteral calculi, tumors, blood clots, or any urethral obstruction. Another noteworthy fact is that a unilateral obstruction may not always present as AKI, especially if the obstruction is gradual such as a tumor, because a normal working contralateral kidney may compensate for the function of the affected kidney. Therefore, the most common etiology of post-renal AKI is bladder outlet obstruction.

AKI is very commonly seen in patients admitted to the hospital. In the United States, 1% of all hospital admissions have AKI on admission. It is often an important factor in making the decision to hospitalize for other conditions, if not being the sole reason for hospitalization. During hospitalization, the approximate incidence rate of acute kidney injury is 2% to 5% and it develops in up to 67% of patients admitted in the intensive care unit. AKI is one of the most clinically impactful diseases since it affects patient management to a great extent in terms of the treatment options for their primary disease. Most drugs or procedures that use contrast media may need to be delayed due to co-existent AKI. Most of the drugs are excreted by the kidney, and dosages might need to be adjusted on account of the reduced renal function. Sometimes, it may even necessitate frequent monitoring of drug levels, for example, vancomycin levels. Furthermore, a huge percentage, approximately 95%, of nephrologist's consultations are related to AKI. AKI is thus an important contributor to more extended hospital stays and patient morbidity.

Treatment: With the exception of post-renal AKI, most cases are an overlap between pre-renal and acute tubular necrosis type of AKI. The best way to determine if the AKI is pre-renal or not is a fluid challenge. If the clinical scenario does not contradict it, all patients with acute renal dysfunction should receive a fluid challenge. They require close monitoring of urine output and renal function. If the renal function improves with fluid that is the best indicator of a pre-Renal AKI. Acute tubular necrosis is very slow to recover and can take weeks to months for complete recovery of renal function. It may not normalize at all sometimes. Diuretics may be required during the oliguric phase of ATN if significant volume overload develops. Another important thing to consider for these patients is to avoid any further insult to the kidneys, such as nephrotoxic drugs. The doses of all medications need to be renally adjusted once a patient develops AKI. Another vital step is to limit the dietary ingestion of potassium and phosphorus.

If hyperkalemia develops, it needs to be managed in a robust manner because, in AKI patients, it can be catastrophic. Approaches to lower potassium in the body include:

1. Dietary restriction
2. Insulin, IV dextrose and beta-agonists
3. Potassium-binding resins
4. Gluconate to stabilize cardiac membrane
5. Dialysis for nonresponsive hyperkalemia Some AKI patients would tend to develop volume overload, which should be corrected as early as possible to avoid pulmonary and cardiac complications. Euvolemic state can be achieved with the help of furosemide, which is a cornerstone in the management of such patients. Usually, high doses of IV furosemide are needed to correct volume overload in AKI patients; however, it plays no role in the conversion of oliguric AKI to non-oliguric AKI.

Sometimes, AKI may need short-term renal replacement therapy until the kidney function recovers. Dialysis is usually required to manage the complications of AKI, such as severe and nonresponsive hyperkalemia, uremic pericarditis, and pulmonary edema. This is seen especially in the oliguric phase of acute tubular necrosis, where the patient is prone to develop multiple electrolyte and acid-base abnormalities as well as fluid overload. When required, dialysis in this setting is usually performed through a double-lumen central venous catheter. Continuous renal replacement therapy can also be utilized in patients who cannot tolerate hemodialysis due to hypotension. It is a much slower, continuous type of dialysis. Correction of some of the metabolic abnormalities, along with dialysis, may be required. Metabolic acidosis is one such instance where systemic administration of citrate or bicarbonate is often required to maintain a suitable blood pH. The requirement for renal replacement therapy should be reevaluated in these patients daily while they are hospitalized and at least weekly thereafter until the kidney function is stable. Renal replacement therapy is usually required for the short-term ranging from a few days to a few weeks in most cases; however, acute tubular necrosis can take up to months to recover and may, therefore, require intermittent hemodialysis support during that time.

There are certain specific treatments that are required for acute kidney injury in specific circumstances, such as administration of vasoactive medications and colloids for treatment of hepatorenal syndrome and cautious diuresis in cardiorenal syndrome. Acute kidney injury from various glomerulonephritides may require immunosuppressive medications for treatment. Acute interstitial nephritis, which does not recover with supportive care, may benefit from a trial of steroids. Post renal obstruction may need to be relieved operatively in certain situations. For example, benign prostatic hypertrophy may require surgical relief of bladder outlet obstruction. Urethral calculi may require stinting and lithotripsy.

It is also important to note that in a certain situation, the risk of acute kidney injury may be decreased by taking some measures. For example, in high-risk patients such as those with compromised renal function at baseline, it may be beneficial to administer peri-procedure intravenous fluids to prevent contrast-induced nephropathy when performing cardiac catheterization.

The management of AKI hinges on identification and treatment of the underlying cause. The main objectives of initial management are to prevent cardiovascular collapse and death and to call for specialist advice from a nephrologist. In addition to treatment of the underlying disorder, management of AKI routinely includes the avoidance of substances that are toxic to the kidneys, called nephrotoxins. These include NSAIDs such as ibuprofen or naproxen, iodinated contrasts such as those used for CT scans, many antibiotics such as gentamicin, and a range of other substances.

Monitoring of kidney function, by serial serum creatinine measurements and monitoring of urine output, is routinely performed. In the hospital, insertion of a urinary catheter helps monitor urine output and relieves possible bladder outlet obstruction, such as with an enlarged prostate.

Prerenal: In prerenal AKI without fluid overload, administration of intravenous fluids is typically the first step to improving kidney function. Volume status may be monitored with the use of a central venous catheter to avoid over- or under-replacement of fluid.

If low blood pressure persists despite providing a person with adequate amounts of intravenous fluid, medications that increase blood pressure (vasopressors) such as norepinephrine, and in certain circumstances medications that improve the heart's ability to pump (known as inotropes) such as dobutamine may be given to improve blood flow to the kidney. While a useful vasopressor, there is no evidence to suggest that dopamine is of any specific benefit and may in fact be harmful.

Intrinsic: The myriad causes of intrinsic AKI require specific therapies. For example, intrinsic AKI due to vasculitis or glomerulonephritis may respond to steroid medication, cyclophosphamide, and (in some cases) plasma exchange. Toxin-induced prerenal AKI often responds to discontinuation of the offending agent, such as ACE inhibitors, ARB antagonists, aminoglycosides, penicillins, NSAIDs, or paracetamol.

The use of diuretics such as furosemide, is widespread and sometimes convenient in improving fluid overload. It is not associated with higher mortality (risk of death), nor with any reduced mortality or length of intensive care unit or hospital stay.

Postrenal: If the cause is obstruction of the urinary tract, relief of the obstruction (with a nephrostomy or urinary catheter) may be necessary.

Renal replacement Therapy: Renal replacement therapy, such as with hemodialysis, may be instituted in some cases of AKI. Renal replacement therapy can be applied intermittently (IRRT) and continuously (CRRT). Study results regarding differences in outcomes between IRRT and CRRT are inconsistent. A systematic review of the literature in 2008 demonstrated no difference in outcomes between the use of intermittent hemodialysis and continuous venovenous hemofiltration (CVVH) (a type of continuous hemodialysis). Among critically ill patients, intensive renal replacement therapy with CVVH does not appear to improve outcomes compared to less intensive intermittent hemodialysis. However, other clinical and health economic studies demonstrated that, initiation of CRRT is associated with a lower likelihood of chronic dialysis and was cost-effective compared with IRRT in patients with acute kidney injury.

Differential diagnosis: Acute kidney injury can occur in patients with preexisting chronic renal failure therefore it is crucial to make every effort to preclude all the reversible factors. The best indicator of reversibility is the rate at which the renal function declines, for instance, accelerated worsening of renal function should prompt the search for the cause. Differentials to be considered in AKI include:
1. Renal calculi
2. Sickle cell anemia
3. Chronic renal failure
4. Dehydration
5. Gastrointestinal bleeding
6. Heart failure
7. Urinary tract infection
8. overloading
9. Diabetic ketoacidosis
10. Urinary obstruction Treatment of AKI One main goal of the suggested treatment is to prevent further damage to the kidneys due to a severe cytokine reaction (cytokine storm) that results from the varying causes of AKI. Based on our research, it does not matter what etiology precipitated the acute kidney injury. The treatment goal will be to mitigate unnecessary cytokine damage to the kidney while the initiating factor is addressed. Inhaled anesthetic may be used to suppress the neural acute overproduction of substance P.

An inhaled anesthetic is a chemical compound possessing general anesthetic properties that can be delivered by inhalation. Other inhaled anesthetics may be used to suppress the neutrally controlled production of substance P. The inhaled anesthetics must be safe for patients to inhale. Such inhaled anesthetics may include, but not be limited to, halothane, isoflurane, sevoflurane, desflurane, nitrous oxide, xenon, or a combination thereof. The inhaled anesthetics are subclassified as either volatile or non-volatile. The volatile anesthetics (e.g., halothane, isoflurane, sevoflurane and desflurane) are liquids at room temperature and require the use of vaporizers for inhalational administration. The non-volatile anesthetics (e.g., nitrous oxide and xenon) are in gas form at room temperature. The inhaled anesthetics described in the embodiments of the present disclosure do not encompass anesthetics (e.g., barbiturates, ketamine, propofol) administered by injections such as an intravenous injection. It does not cause respiratory depression, oversedation, or irritation of the lungs at effective dosages with little or no side effects. Other aforementioned inhaled anesthetics can be included in the dosage or only the specified composition can be used. Other inhalants can be included in the above-compositions such as for other purposes.

The inhaled anesthetics are well-known for their central sedative effects such as conscious sedation used in dentistry at lower concentrations to general anesthesia at higher concentrations. Studies show they are also able to suppress the production of the tachykinins (substance P, glutamate, and CGRP) in the spinal and vagus sensory ganglia. The half-life of the tachykinins is seconds to minutes, so the effect is almost instantaneous. Unlike the central sedative effect, which lasts only minutes after cessation of use, the substance P suppression in the ganglia lasts for 4-6 hours.

When sensory nerves are damaged by an infection or injury, the neurons and the neurostructural cells around them (astrocytes, glial cells, and satellite) produce substance P, glutamate, and CGRP in response. The glutamate causes sensory hypersensitivity and substance P activates receptors on immune cells producing the vast array of cytokines to fight infection or repair damage.

In the present disclosure, Applicant currently believes the most preferable anesthetic to use is nitrous oxide. It does not cause respiratory depression, over sedation, or irritation of the lungs at effective dosages with little or no side effects. The inhaled dosage can be from 1% nitrous oxide/99% oxygen to 70% nitrous oxide/30% oxygen depending on individual needs and sensitivity. Clinical indications suggest that 40% nitrous oxide/60% oxygen to 50% nitrous oxide/50% oxygen would be optimal. Time of inhalation would vary from one minute to one hour with 20 minutes being the optimal time frame. A longer time may be used if necessary. For example, the nitrous oxide and oxygen may be administered to an adult who weighs about 150 lbs. for about between 1 minute and about 1 hour every about 4-6 hours; or for about 20 minutes every about 4-6 hours. The nitrous oxide and oxygen may be administered by continuous administration over the period of time. Duration of substance P suppression can be from 1 minute to 12 hours with average cases of 4-6 hours of substance P suppression. The length of treatment to suppress the severe cytokine reaction will vary and be influenced by the time to medically correct the initiating factor. The nitrous oxide mechanism is suppression of substance P in the peripheral spinal and vagus ganglia. The amount of nitrous oxide or inhaled anesthetics used, duration of administration, and length of effectiveness will have to be titrated to the individual. For children, adjustments will have to be made for age and body weight. Other inhaled anesthetics may have to be used at a different oxygen % than the nitrous oxide to produce effective clinical results. Other aforementioned inhaled anesthetics can be included in the dosage or only the specified composition can be used. Other inhalants can be included in the above-compositions such as for other purposes.

If side effects from too much substance P suppression nitrous oxide use occur, then inhalation may be reduced or eliminated. Before, during, and after the provision of the inhaled nitrous oxide and oxygen, blood tests may be done to monitor and assess the patient's cytokine level including a substance P level and a viral load. In addition, before, during and after the inhalation of nitrous oxide and oxygen, a blood oxygen level and a pulse may be monitored and assessed.

In some embodiments, a composition administered to a patient consists of nitrous oxide and oxygen.

In some embodiments, a pharmaceutically active composition contained in a composition administered to a patient consists of nitrous oxide and oxygen.

The composition may additionally include a pharmaceutically inactive composition such as a pharmaceutically inactive excipient, stabilizer and/or carrier.

Case Study #1

A 62-year-old adult female with chronic kidney disorder had kidney function which had been steadily declining for approximately 18 years. The patient's weight was about 140 lbs, and was in generally good health except for the kidney failure. She also had migraines and lower back pain. On Jan. 15, 2021, the patient was treated with the injection technique described in the present disclosure all dermatomes with botulinum toxin Type A. The injections covered the trigeminal, cervical, thoracic, lumbar, and sacral dermatomes, providing for 60 units total. Her kidney function was 52% at her doctor visit on December 15th. Six weeks after treatment at her next doctor visit her kidney function was 91% based on doctor blood testing. Patient reported that it had never improved before the treatment.

In some embodiments, a composition administered to a patient comprises nitrous oxide and oxygen. The composition may further comprise one or more additional pharmaceutically active ingredients. The composition may further comprise one or more additional pharmaceutically inactive ingredients.

Case Study #2

A 62-year-old female was diagnosed with chronic kidney failure 2 years ago. Her kidney function has been progressively decreasing over the last 2 years. The patient weighted about 130 lbs and she has multiple other health issues including migraines, fibromyalgia, diabetes, liver failure, COPD, and back pain. In January, the kidney function was at 53%. On March 15th, she was treated with botulinum toxin in her trigeminal, cervical, lumbar, sacral, and thoracic areas with our injection techniques providing for 60 units total. On May 1st, kidney function was 60% based on doctor blood testing. This was the first time it had improved according to the patient.

Nitrous oxide or any inhaled anesthetic can be used to mitigate the extreme cytokine reaction in some kidney injury events. This will prevent cytokine mediated damage to the kidney while the precipitating event is addressed. Botulinum toxin can be used to mitigate the chronic inflammation that is responsible for CKD's slow progressing damage to and loss of function of the kidney that can lead to kidney failure.

Further patient testing is being pursued using botulinum toxin and nitrous oxide.

The description of ranges also describes the ranges within the specifically described range and describes individual numerical points for treatment. The described ranges are inclusive of endpoints in the range.

It should be understood that the present description of embodiments of the invention includes a composition for use in treating the conditions. For example, botulinum toxin for use in treating chronic kidney disease in a patient in a need thereof.

It should be understood that the above description of embodiments of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method of treating chronic kidney disease and other chronic renal conditions that have resulted from the overproduction of cytokines in a patient in need thereof, comprising:
   administering a botulinum toxin to the patient by subcutaneous or intradermal injection, 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the spine, 1-4 units to and/or around the vicinity of a lumbar nerve, lateral to the spine, and/or 1-4 units to and/or around the vicinity of a sacral nerve, lateral to the spine.

2. The method of claim 1, wherein the trigeminal nerve is selected from the group consisting of an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, a lesser occipital nerve, a greater occipital nerve, or a combination thereof.

3. The method of claim 1, wherein the cervical nerve is selected from the group consisting of a c-2 nerve, c-3 nerve, c-4 nerve, c-5 nerve, c-6 nerve, c-7 nerve, c-8 nerve, or a combination thereof.

4. The method of claim 1, wherein the thoracic nerve is selected from the group consisting of t-2 to t-3, t-5 to t-6, t-7 to t-9, t-10 to t-12, or a combination thereof.

5. The method of claim 1, wherein the sacral nerve is selected from the group consisting of s-1 to s-2, s-3 to s-4, and/or s-4 to s-5, or a combination thereof.

6. The method of claim 1, wherein a therapeutically effective amount of the botulinum toxin administered is between about 1 unit and about 150 units.

7. The method of claim 1, wherein a therapeutically effective amount of the botulinum toxin administered is between about 50 units and about 100 units.

8. The method of claim 1, wherein a total dosage of the botulinum toxin to an adult who weighs about 150 lbs. is less than or equal to about 50 units, and the total dosage of the botulinum toxin in an adult is adjusted for weight, and wherein a total dosage of the botulinum toxin in a child over about 5 years old and a toddler about from 1 to 5 years old is adjusted for age, weight or a combination thereof.

9. The method of claim 1, wherein a total dosage of the botulinum toxin to an adult who weighs about 150 lbs. is higher than or equal to about 50 units and lower than or equal to 150 units, and the total dosage of the botulinum toxin in an adult is adjusted for weight.

10. The method of claim 1, wherein each of the subcutaneous or intradermal injection is bilateral.

11. The method of claim 1, wherein the patient is administered 2-4 units to and/or around the vicinity of an ophthalmic, maxillary, and/or mandibular nerve of the trigeminal nerve, 2-4 units to and/or around the vicinity of the c-2 to c-3, c-4 to c-6, and/or c-7 to c-8 of the cervical nerve, about one-inch lateral to the patient's spine, 2-4 units to and/or around the vicinity of the t-2 to t-3, t-5 to t-6, t-7 to t-9, and/or t-10 to t-12 of the thoracic nerve, about one inch lateral to the patient's spine, 2-4 unit to and/or around the vicinity of the 1-1 to 1-2, 1-2 to 1-3, and/or 1-4 to 1-5 of the lumbar nerve, about one inch lateral to the patient's spine, and/or 2-4 units to and/or around the vicinity of the s-1 to s-2, s-3 to s-4, and/or s-4 to s-5 of the sacral nerve, about one inch lateral to the patient's spine.

* * * * *